United States Patent [19]

Kawauchi et al.

[11] Patent Number: 5,698,528
[45] Date of Patent: Dec. 16, 1997

[54] SUBSTANCE IT-62-B AND MEDICINAL COMPOSITION CONTAINING THE SAME

[75] Inventors: Takashi Kawauchi, Naruto; Toru Sasaki, Tokushima; Hiroshi Matsumoto, Tokushima; Toshio Otani, Tokushima, all of Japan; Ru-Xian Chen; Ming-Yu Huang, both of Beijing, China; Ken-ichiro Yoshida, Tokushima, Japan

[73] Assignee: Taiho Pharmaceutical Co., Ltd., Tokyo, Japan

[21] Appl. No.: 601,023

[22] PCT Filed: Jul. 12, 1995

[86] PCT No.: PCT/JP95/01384

§ 371 Date: Feb. 23, 1996

§ 102(e) Date: Feb. 23, 1996

[87] PCT Pub. No.: WO96/02659

PCT Pub. Date: Feb. 1, 1996

[30] Foreign Application Priority Data

Jul. 14, 1994 [JP] Japan ................... 6-162037

[51] Int. Cl.$^6$ ............. A61K 31/71; C07H 15/252; C12P 19/56

[52] U.S. Cl. ............. 514/34; 435/78; 536/6.4; 536/16.8

[58] Field of Search ............. 435/78; 536/6.4, 536/16.8; 514/34

[56] References Cited

U.S. PATENT DOCUMENTS 5,147,860  9/1992  Kanamaru et al. ............ 514/34

Primary Examiner—Herbert J. Lilling
Attorney, Agent, or Firm—Sughrue, Mion, Zinn, Macpeak & Seas, PLLC

[57] ABSTRACT

A substance IT-62-B represented by the following formula (1):

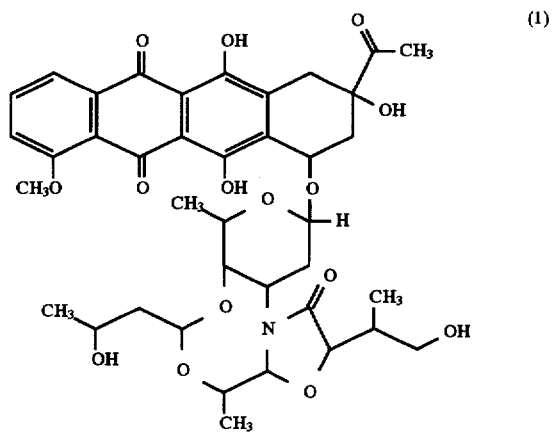

a production process thereof, a medicinal composition comprising the compound as an active component, and methods of treating an infectious disease caused by bacteria and a tumor, in which such a substance is administered.

The compound according to the invention has good antibacterial activities against gram-positive bacteria and some of gram-negative bacteria, and also possesses excellent antitumor activities against tumors such as human nasopharyngeal carcinoma, and is hence useful as a medicine.

9 Claims, 3 Drawing Sheets

SUBSTANCE IT-62-B AND MEDICINAL COMPOSITION CONTAINING THE SAME

TECHNICAL FIELD

The present invention relates to a new substance IT-62-B, a production process thereof, a medicinal composition containing such a substance and methods of treating an infectious disease caused by bacteria and a tumor, in which such a substance is administered.

BACKGROUND ART

It has heretofore been known that microorganisms produce various substances each having wide features from the viewpoint of chemical structure, and pharmacological activities such as antibacterial activities and antitumor activities.

Accordingly, it is an object of the present invention to provide a substance having far excellent pharmacological activities by using microorganisms.

DISCLOSURE OF THE INVENTION

In view of the foregoing circumstances, the present inventors have isolated many microorganisms from natural soils to retrieve their capability of producing substances having useful pharmacological activities. As a result, it has been found that a *Streptomyces sp.* strain IT-62 belonging to genus Streptomyces produces a novel substance IT-62-B exhibiting excellent antibacterial activities and antitumor activities, thus leading to completion of the present invention.

TAN-1120 has been reported as a streptomyces-produced substance having a structure similar to that of the compound according to the present invention (Japanese Patent Application Laid Open No. 288892/1990). However, the substance of the present invention is a novel compound having a structure that oxazolidine ring has been additionally ring-condensed.

Namely, the present invention is directed to a substance IT-62-B represented by the following formula (1):

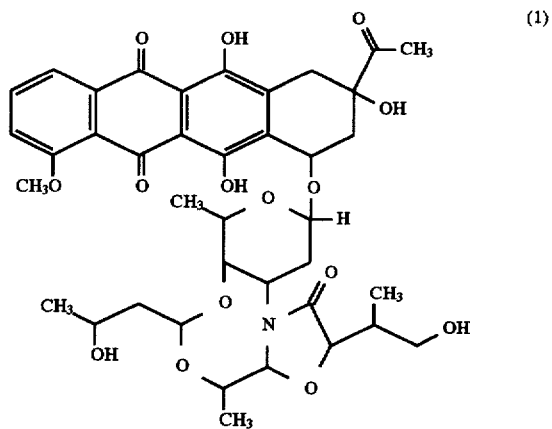

(1)

The present invention is also directed to a process for producing the substance IT-62-B, which comprises culturing a microorganism belonging to genus Streptomyces and having capability of producing the substance IT-62-B to produce and accumulate such a compound in the culture fluid and to separate the compound.

The present invention is further directed to a medicine, an antibacterial agent and an antitumor agent each comprising the substance IT-62-B as an active component.

The present invention is still further directed to a medicinal composition comprising the substance IT-62-B and a pharmaceutically permissible carrier.

The present invention is yet still further directed to methods of treating a bacterial infectious disease and a tumor, which each comprise administering an effective amount of the substance IT-62-B to a patient.

The present invention is yet still further directed to use of the substance IT-62-B for a medicine.

BEST MODE FOR CARRYING OUT THE INVENTION

Figure 1:
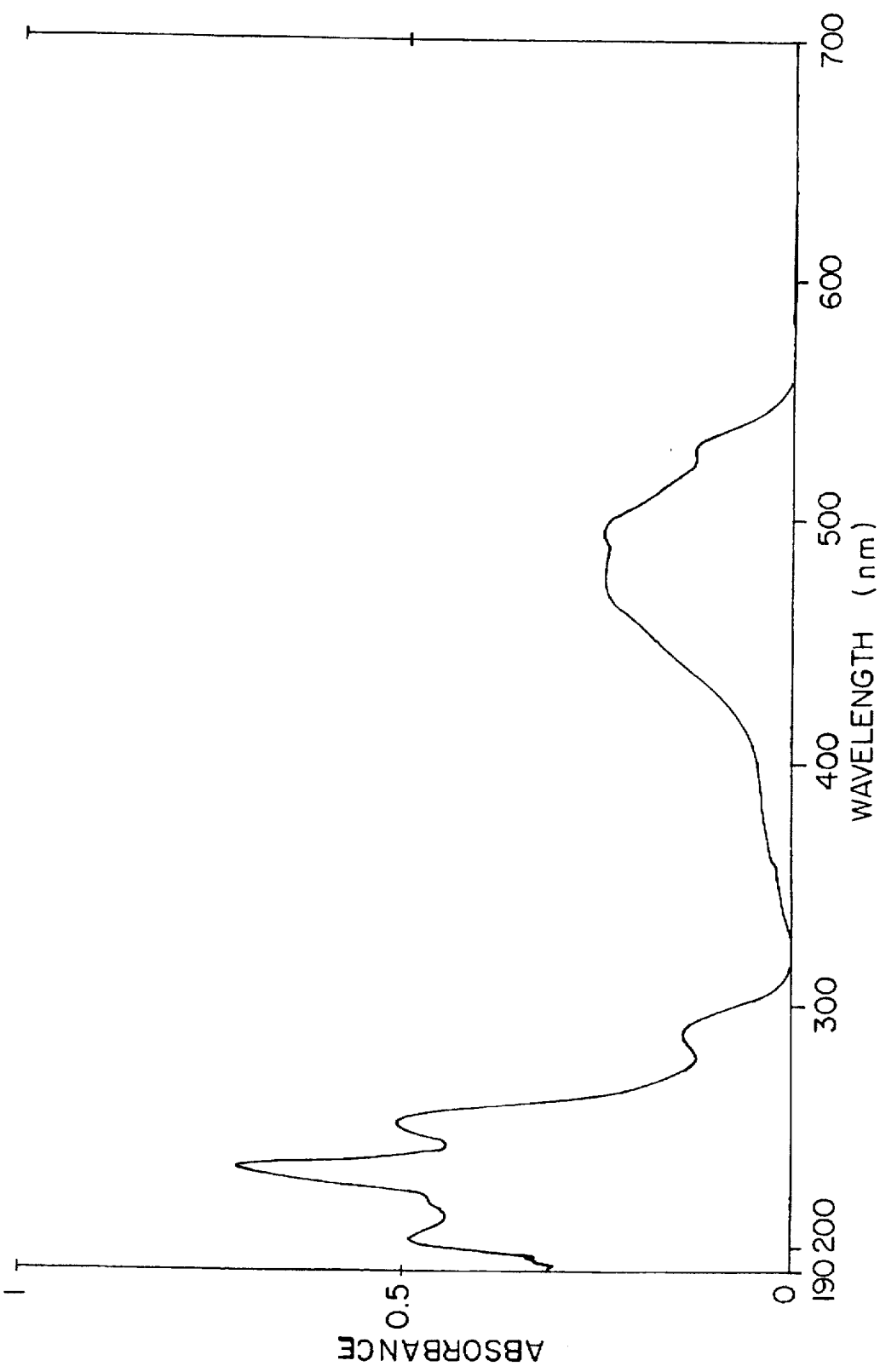
FIG. 1 illustrates an ultraviolet absorption spectrum of a substance according to the present invention obtained in Example 1.

The substance IT-62-B according to the present invention is represented by the formula (1), and there are isomers based on asymmetric carbon atoms in this compound. However, the present invention includes all of these isomers and mixtures thereof. The substance according to the present invention may exist in the form of a hydrate, and the present invention also include such a hydrate.

The substance IT-62-B according to the present invention can be produced by culturing a strain having capability of producing this substance (hereinafter referred to as "substance IT-62-B-producing strain") under suitable conditions.

The substance IT-62-B-producing strain include microorganisms belonging to genus Streptomyces. As an illustrative example thereof, may be mentioned *Streptomyces sp.* strain IT-62. This strain is isolated from a soil of the Uigurian province in the People's Republic of China by the present inventors, and was deposited as identification of the microorganism "Strain IT-62", accession number FERM BP-4666 in National Institute of Bioscience and Human-Technology, Agency of Industrial Science and Technology, Japan on May 13, 1994.

The microbiological characteristics of the strain IT-62 investigated in accordance with the method described in International Journal of Systematic Bacteriology, 16(3), 313–340, 1960 is as follows:

(a) Morphology:
  Branching of sporulating hyphae: Simple branching.
  Form of sporulation: Straight or flexibilis, or sometime hook, spore form is cylindrical shape.
  Number of spores: 10 to 50 or more spores.
  Spore surface: Smooth.
  Size of spore: 0.5–0.8×0.7–1.1 μm.
  Presence of flagellate: Not present.
  Presence of sporangia: Not present.
  Attachment site of sporophores: Aerial mycelium.
  Possession of sclerotium-forming ability: No possession.
(b) Culture characteristics on various media:

Cultural characteristics of strain IT-62 on various media are shown in Table 1. Taxonomic colors were indicated in accordance with "Standard Color Chart A, 1981" under the supervision of *The Japan Color Research Institute*. Incidentally, more detailed colors were additionally given in parentheses in terms of color codes in accordance with "The Color Harmony Manual, the fourth edition, 1958" published by Container Corporation of America.

The substance IT-62-B according to the present invention can be produced, for example, by culturing various sub-

TABLE 1

| Medium | Growth condition | Aerial mycelium | Substrate mycelium | Soluble pigment | Reverse |
|---|---|---|---|---|---|
| Sucrose-nitrate agar | Poor | None | Colorless | None | Colorless |
| Glucose-asparagine agar | Good | None | Vivid reddish orange (6pa–6pc) | Orangish | Vivid reddish orange (6pa–6lc) |
| Glycerol-asparagine agar (ISP medium No. 5) | Good | Whitish–pale yellow (2ca) | Olive yellow (2le) | None | Olive yellow (2le) |
| Inorganic salts-starch agar (ISP medium No. 4) | Good | Pale yellowish pink (4ca) | Strong reddish orange (5le) | Orangish | Strong reddish orange (5le) |
| Tyrosine agar (ISP medium No. 7) | Good | Yellowish white (3cb)–yellowish gray (2ec) | Light yellowish brown (3ie) | Brownish | Yellowish brown (3pg, 3ne) |
| Oat meal agar (ISP medium No. 3) | Good | Yellowish gray (2cb–lec) | Light reddish orange (5lc) | Orangish | Light reddish orange (4ne) |
| Yeast extract-malt extract agar (ISP medium No. 2) | Good | Whitish, scant | Strong reddish orange (6ne) | Orangish | Strong reddish orange (6ne) |
| Nutrient agar | Moderate | Whitish, scant | light reddish orange (5lc) | Orangish | light reddish orange (4ic) |
| BENNET'S agar | Good | None | Vivid red (6½pc) | Orangish | strong red (6pc) |

(c) Physiological characteristics:

Temperature range for growth: The strain exhibits good growth in the temperature range of 20°–37° C.

Liquefaction of gelatin (glucose-peptone-gelatin medium, 27° C.): Negative.

Liquefaction of gelatin (simple gelatin medium, 20° C.): Positive.

Coagulation of milk (37° C.): Positive.

Peptonization of milk (37° C.): Positive.

Production of a melanoid pigment: Negative on tyrosine agar (ISP medium No.7), peptone-yeast extract-iron agar (ISP medium No.6) and tryptone-yeast extract medium (ISP medium No.1).

Production of hydrogen sulfide [medium obtained by adding 0.5% yeast extract to peptone-yeast extract-iron agar (ISP medium No.6)]: Positive.

Hydrolysis of starch (starch-inorganic salt agar, ISP medium No.4): Positive.

Reduction of nitrate (1% potassium nitrate-containing bouillon, ISP medium No.8): Positive.

Decomposition of cellulose: Negative.

(d) Utilization of carbon sources (Pridham-Gottlieb's medium, ISP medium No.9):

This strain utilizes D-glucose, L-arabinose, D-xylose, D-fructose, D-mannitol, D-galactose, soluble starch, dextrin, glycerol and maltose, but not utilize inositol, sucrose, L-rhamnose, raffinose and salicin.

(e) Chemotaxonomy:

The whole cell hydrolysates were analyzed by the high performance liquid chromatography described in "Experimental Method for Identifying Actinomycetes— Qualitative Analysis, Quantitative Analysis of Mycelial Components by HPLC, pp. 1–8, 1989" edited by The Japan Society for Actinomycetes Japan. As a result, LL-diaminopimelic acid was detected.

In view of the fact that the strain according to the present invention has the above-described microbiological characteristics, in particular, those characteristics that aerial mycelia having many spore chains are formed, the amino acid in the cell wall hydrolysates contains LL-diaminopimelic acid, and neither flagellate nor sporangia are formed, it is apparent that the strain belongs to genus Streptomyces. Accordingly, this strain was determined to be designated "Streptomyces sp. IT-62".

stance IT-62-B-producing microorganisms belonging to genus Streptomyces such as the strain IT-62 or variants thereof in their suitable media, then separating crude extracts containing the substance of the present invention from the culture media and further isolating the substance IT-62-B from the crude extracts to purify it.

The culture of the microorganism is basically carried out in accordance with the culture of the general microorganisms. It is, however, generally preferred to perform the culture under aerobic conditions such as a shaking culture process by liquid culture or aerobic spinner culture process.

The medium used in the culture may be some of media so far as it contains nutrients which can be utilized by the substance IT-62-B-producing bacteria. Some of various synthetic media, semisynthetic media, natural media and the like may be used. As a carbon source for the medium, glucose, sucrose, fructose, glycerol, dextrin, starch, molasses, corn steep liquor, organic acids and the like may be used either singly or in any combination thereof; and as a nitrogen source, organic nitrogen sources such as Pharma media, peptone, meat extract, yeast extract, soybean powder, casein, amino acids and urea, and inorganic nitrogen sources such as sodium nitrate and ammonium sulfate may be used either singly or in any combination thereof. To the medium, sodium salts, potassium salts, magnesium salts, phosphates, heavy metal salts and/or the like may be suitably added if needed.

If foaming is marked during the culture, antifoaming agents, such as vegetable oils, for example, soybean oil and linseed oil, higher alcohols such as octadecanol, tetradecanol and heptadecanol, and various silicon compounds may also be suitably added to the medium.

It is preferable to adjust the pH of the medium near to neutrality. The incubation temperature may preferably be maintained at a temperature for the good growth of the substance IT-62-B-producing strain, usually 20°–37° C., particularly preferably about 25°–30° C. The incubation time may preferably be 4–7 days for both liquid shaking culture and aerated agitating-culture.

As described above, the various incubation conditions may be suitably changed according to the kind and nature of the microorganism used, external conditions and the like, and optimum conditions may be selected from and controlled within the above ranges depending thereon.

The separation of the crude extract containing the substance IT-62-B from the culture fluid can be carried out in accordance with the general method for collecting fermentation products. For example, means such as solvent extraction, partition and absorption chromatography and crystallization may be used either singly or in combination thereof in any suitable order. More specifically, since the substance IT-62-B produced by the above culture is principally present in the cultural mycelia, filtration, centrifugation or the like is first performed to separate a filtrate of the culture fluid and solid mycelia from each other. The resultant solid mycelia containing the substance IT-62-B are extracted with a solvent such as methanol or acetone to dissolve the substance IT-62-B out of the mycelia. Then, the solvent is removed under reduced pressure, whereby a crude concentrate containing the substance IT-62-B can be obtained. An organic solvent immiscible with water, such as ethyl acetate, chloroform or butanol is added to this crude concentrate to extract the substance IT-62-B with organic solvent. After the thus-obtained solvent layer is added with Glauber's salt to dehydrate, the solvent is removed under reduced pressure, whereby a crude extract containing the substance IT-62-B can be obtained. As needed, there may be adopted such means as its pH is adjusted with sodium hydroxide or hydrochloric acid, industrial sodium chloride is added to enhance efficiency of extraction, and the formation of an emulsion is prevented.

In order to isolate and purify the substance IT-62-B from the crude extract, there may be used usual means for isolation and purification of a fat-soluble low-molecular weight substance, for example, a variety of adsorption chromatography on adsorbents such as silica gel, alumina and macroporous and nonionic adsorption resins, and reversed phase chromatography making use of ODS-bonded silica gel or the like. Of these, chromatography on silica gel using chloroform, or a mixed solvent system such as chloroform/methanol, chloroform/methanol/benzene or toluene/methanol, as an eluent, and reversed phase chromatography using a mixed solvent system such as acetonitrile/water or methanol/water in elution are particularly preferred. If further purification is required, the above-described chromatography may be conducted repeatedly or in suitable combination with gel filtration chromatography on Sephadex LH-20 (product of Pharmacia AB) using chloroform, methanol or the like as an eluent, or the like, thereby obtaining the substance IT-62-B with high purity.

The identification of the substance IT-62-B during the purification process may preferably be performed by a bioassay using a microorganism on which a growth inhibiting effect is detected by this substance, for example, *Micrococcus luteus* ATCC 9341, a method of determining the cytotoxic effect on an established culture cell line (KB cell line) derived from human nasopharyngeal carcinoma and a detecting method using high performance liquid chromatography in combination.

With respect to the pharmacological administration form in the case where the substance IT-62-B purified in the above described manner is used as a medicinal composition, there may be used any of oral preparations such as tablets, capsules, powders, granules, fine granules, solutions, pills, emulsions and suspensions; and parenteral preparations such as injections, suppositories, ointments, plasters, poultices, aerosols and ophthalmic solutions. The preparations of these administration forms can be formulated respectively in accordance with the conventional formulation methods known by those skilled in the art.

In the case where a solid oral preparation is formulated, it is only necessary to add an excipient, and optionally a binder, disintegrator, lubricant, colorant, flavor and/or the like to the active component according to the present invention, and then form the mixture into tablets, capsules, powder, granules, fine granules or the like in accordance with a method known per se in the art. As examples of the excipient include lactose, sucrose, starch, talc, magnesium stearate, crystalline cellulose, methylcellulose, carboxymethylcellulose, glycerol, sodium alginate and gum arabic. Examples of the binder include polyvinyl alcohol, polyvinyl ether, ethylcellulose, gum arabic, shellac and sucrose. Examples of the lubricant include magnesium stearate and talc. Besides, those conventionally known may be used as the colorant, disintegrator and the like. The tablets may be coated by the well-known method.

In the case where an injection is prepared, it is only necessary to add a pH adjustor, buffer, stabilizer, isotonicity-imparting agent, local anesthetic and/or the like to the active component according to the present invention, and prepare the mixture into an intravenous, intramuscular, subcutaneous, intracutaneous and intraperitoneal injection. As the pH adjustor and buffer, may be used sodium citrate, sodium acetate, sodium phosphate and the like. As the stabilizer, may be used sodium pyrosulfite, ethylenediaminetetraacetic acid, thioglycolic acid, thiolactic acid and the like.

A suppository can be prepared by adding a base, and optionally a surfactant and/or the like to the active ingredient according to the present invention, and then following a method known per se in the art. As the base, may be used, for example, oil bases such as Macrogol, lanolin, cacao butter, fatty acid, triglycerides and Witepsol (product of Dynamit Nobel Co.).

The amount of the active component according to the present invention to be incorporated in the above-described preparations of the various administration forms may be suitably selected according to dosing route, the age, sex, diseased condition of the patient to be dosed, the kinds of compounds to be incorporated, and other conditions. However, the active component according to the present invention may be dosed in an amount of generally 0.005–20 mg/day at once or in 2–4 installments.

EXAMPLES

The present invention will hereinafter be described more specifically by the following Example and Test Examples. However, this invention is not defined to and by these examples.

Example 1

Production of the substance IT-62-B of the present invention:

(a) Culture process:

One hundred milliliters of a medium (pH 7.2) comprising 0.5% of glucose, 2.4% of soluble starch, 0.3% of beef extract, 0.5% of yeast extract, 0.5% of peptone, 0.4% of corn steep liquor, 0.002% of cobalt chloride and 0.4% of calcium carbonate were poured into a 500-ml Erlenmeyer flask, sterilized and then inoculated with one platinum loopful of a *Streptomyces sp.* strain IT-62 (Accession Number FERM BP-4666) to conduct rotary shaking culture at 27° C. for 2 days (220 rpm, 7-cm throw). Then, 100 ml of a medium (pH 7.2) comprising 0.5% of glucose, 2.5% of dextrin, 2.0% of sesame meal, 0.5% of corn steep liquor, 0.05% of monopotassium hydrogenphosphate, 0.05% of magnesium sulfate, 0.03% of potassium chloride and 0.3% of calcium carbonate was poured into a 500-ml Erlenmeyer flask and sterilized. Thereafter, the seed culture above were added in a proportion of 2% to conduct rotary shaking culture at 27° C. for 5 days (220 rpm, 7-cm throw).

(b) Separation process:

After the culture fluid (40 liters, pH 7.6) obtained in the above process was collected, centrifuged and filtered, the culture mycelia were extracted twice with acetone (5 liters). The resultant acetone extract was concentrated under reduced pressure, and the resultant concentrate was adjusted to pH 8.0 with a diluted aqueous Solution of sodium hydroxide and then extracted twice with ethyl acetate (2 liters). The fraction extracted with ethyl acetate was concentrated under reduced pressure, and the resultant oily substance (11 g) was dissolved in chloroform (40 ml). Precipitate obtained by further adding n-hexane (120 ml) to the solution was washed with n-hexane and then dried, thereby obtaining 2.7 g of a crude extract.

(c) Isolation and purification process:

The above-obtained crude extract was dissolved in chloroform and subjected to column chromatography on silica gel (Silica Gel 60, 4.1 cm in inner diameter×25 cm in length, product of Merck AG) to effect stepwise elution first with chloroform and then with a mixed solvent of chloroform/methanol (50:1 and 25:1 v/v). The eluted active fractions were identified by a bioassay using *Micrococcus luteus* ATCC 9341 to collect active fractions containing the substance IT-62-B. The thus-collected active fractions were distilled, and the residue was dried over to obtain 155 mg of an oily substance.

Seventy-five milligrams of the thus-obtained oily substance were dissolved in chloroform/methanol (1:1 v/v) to subject the solution to gel filtration chromatography (on Sephadex LH-20 (2.0 cm in inner diameter×92 cm in length), product of Pharmacia AB so as to elute with chloroform/methanol (1:1 v/v). Active fractions containing the substance IT-62-B were collected, and the solvent was removed from the thus-collected active fraction, thereby obtaining 26 mg of an oily substance. The thus-obtained oily substance was dissolved in acetonitrile/water (2:3 v/v), subjected to reversed-phase chromatography making use of an ODS-bonded silica gel column on Ultrapack ODS (30–50 μm, 1.0 cm in inner diameter×50 cm in length, product of Yamazen-Co., Ltd.) so as to elute at a flow rate of 1.5 ml/min using acetonitrile/water (2:3 v/v) as an eluent. The eluted active fractions were identified by the bioassay and high performance liquid chromatography to collect active fractions containing the substance IT-62-B. The organic solvent was removed to get the thus-collected active fraction, and the residue was then lyophilized, thereby to obtain 12 mg of the substance IT-62-B as red powder.

The physico-chemical properties of the thus-obtained substance IT-62-B will be described below.

(1) Appearance: Red powder.

(2) Molecular formula:

$C_{39}H_{47}NO_{15}$ (measured by high resolution fast atomic bombardment mass spectrometory. As $C_{39}H_{47}NO_{15}Na$, found: 792.294; calculated: 792.284).

(3) Molecular weight:

769 (measured by fast atomic bombardment mass spectrometory).

(4) Optical rotation:

$[\alpha]_D^{23}$ +360° (c=0.015, methanol).

(5) Ultraviolet absorption spectrum, in methanol solution, $\lambda_{max}$(nm) ($\epsilon$):

233(33100), 251(23400), 289(6600), 480(11300), 495 (11400), 530(6200, sh) (see FIG. 1).

Figure 2:
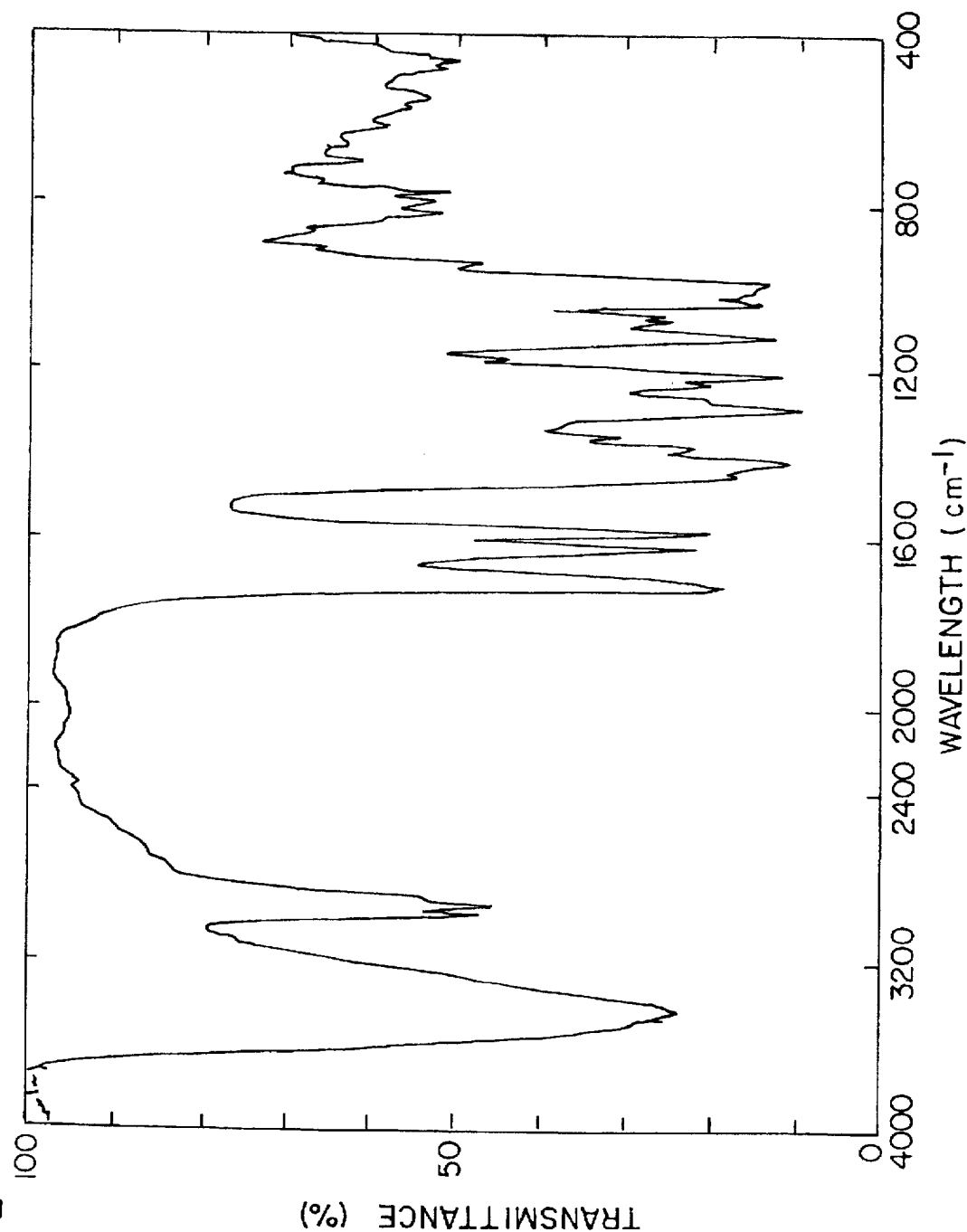
FIG. 2 illustrates an infrared absorption spectrum of the substance according to the present invention obtained in Example 1.

(6) Infrared absorption spectrum, KBr tablet method, $v_{max}$ ($cm^{-1}$):

3435, 2970, 2935, 1710, 1620, 1580, 1415, 1285, 1210, 1120, 1035, 995 (see FIG. 2).

Figure 3:
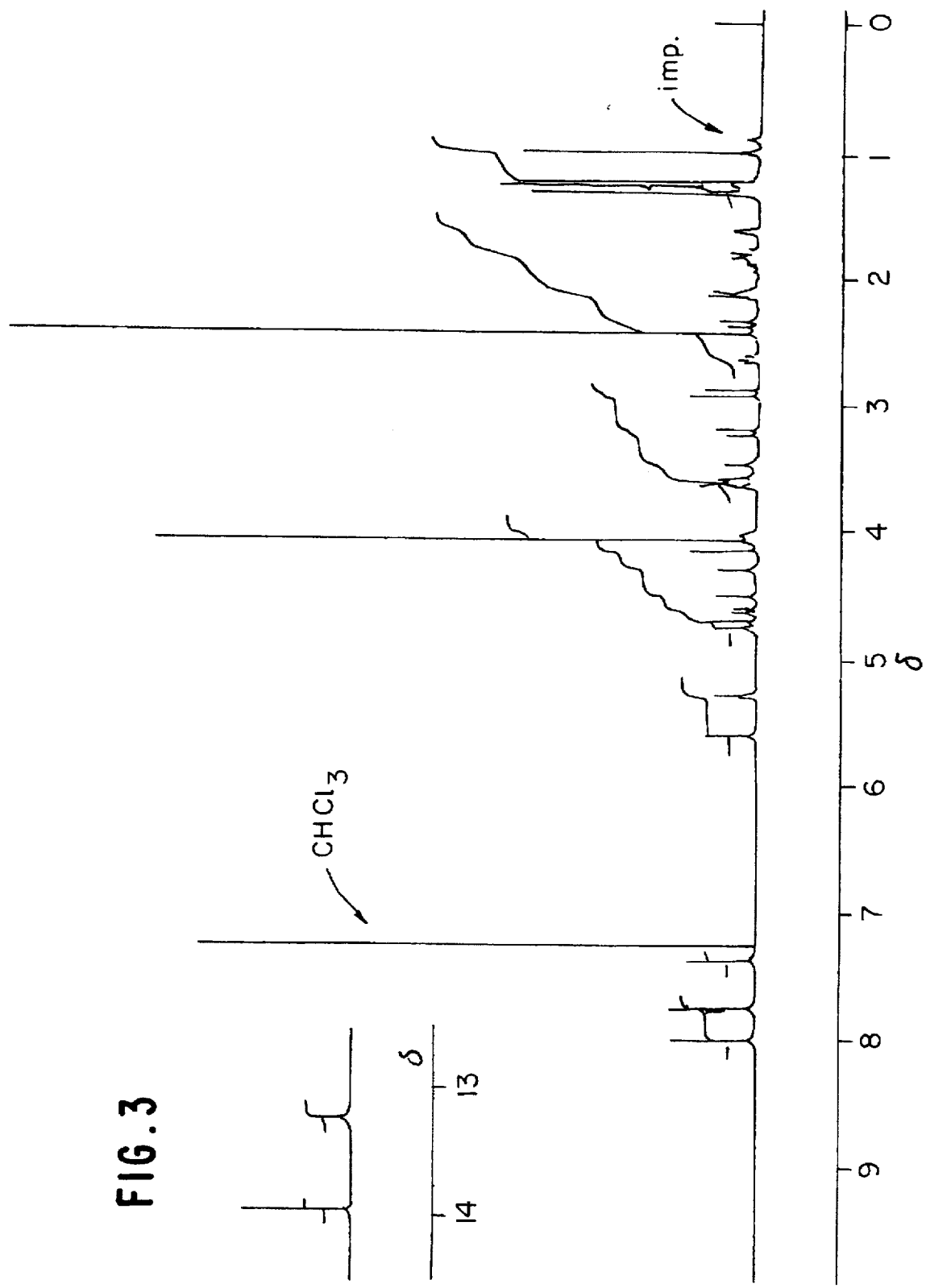
FIG. 3 illustrates a $^1$H-NMR spectrum of the substance according to the present invention obtained in Example 1.

(7) Nuclear magnetic resonance spectrum:

The values of chemical shifts in a 400 MHz $^1$H-NMR spectrum (FIG. 3) and a 100 MHz $^{13}$C-NMR spectrum measured in a deuteriochloroform solution are shown in Tables 2 and 3, respectively.

TABLE 2

| Position | $^1$H (δ) |
|---|---|
| 1 | 8.01,d,8Hz |
| 2 | 7.77,t,8Hz |
| 3 | 7.38,d,8Hz |
| 7 | 5.27,dd,4,1Hz |
| 8 | 2.12,dd,15,4Hz, 2.36,dt,15,1Hz |
| 10 | 2.91,d,19Hz, 3.22,dd,19,1.5Hz |
| 14 | 2.44,s |
| OCH$_3$-4 | 4.07,s |
| OH-6 | 13.94,s |
| OH-9 | 4.49,br.s |
| OH-11 | 13.23,s |
| 1' | 5.60,d,4Hz |
| 2' | 1.61,dd,13.5,4Hz, 2.64,td,13.5,4Hz |
| 3' | 4.61,dd,13.5,4Hz |
| 4' | 3.61,s |
| 5' | 4.29,q,6.5Hz |
| 6' | 1.26,d,6.5Hz |
| 1" | 4.74,dd,7,4Hz |
| 2" | 1.78,ddd,14,9.5,4Hz, 1.85,ddd,14,7,3Hz |
| 3" | 4.03,m |
| 4" | 1.23,d,6Hz |
| 5" | 3.48,dq,8,6.5Hz |
| 6" | 4.70,d,8Hz |
| 7" | 1.31,d,6.5Hz |
| 9" | 4.15,d,4.5Hz |
| 10" | 2.12,m |
| 11" | 3.58,dd,11,7.5Hz, 3.65,dd,11,4.5Hz |
| 12" | 0.98,d,7Hz |

The above positions denote protons situated at the following sites, respectively.

TABLE 3

| Position | $^{13}$C (δ) | Position | $^{13}$C (δ) |
|---|---|---|---|
| 1 | 119.80,d | 1' | 100.67,d |
| 2 | 135.65,d | 2' | 28.70,t |
| 3 | 118.36,d | 3' | 50.41,d |
| 4 | 161.03,s | 4' | 79.18,d |
| 4a | 120.95,s | 5' | 69.51,d |
| 5 | 187.03,s | 6' | 17.17,q |
| 5a | 111.38,s | 1" | 106.53,d |
| 6 | 156.41,s | 2" | 45.64,t |
| 6a | 134.14,s | 3" | 64.38,d |
| 7 | 69.68,d | 4" | 23.97,q |
| 8 | 35.13,t | 5" | 80.37,d |
| 9 | 76.61,s | 6" | 91.03,d |
| 10 | 33.36,t | 7" | 17.17,q |
| 10a | 134.64,s | 8" | 173.18,s |
| 11 | 155.92,s | 9" | 80.20,d |
| 11a | 111.21,s | 10" | 38.02,d |
| 12 | 186.59,s | 11" | 64.21,t |
| 12a | 135.55,s | 12" | 12.44,q |
| 13 | 212.19,s | | |
| 14 | 24.87,q | | |
| OCH$_3$-4 | 56.64,q | | |

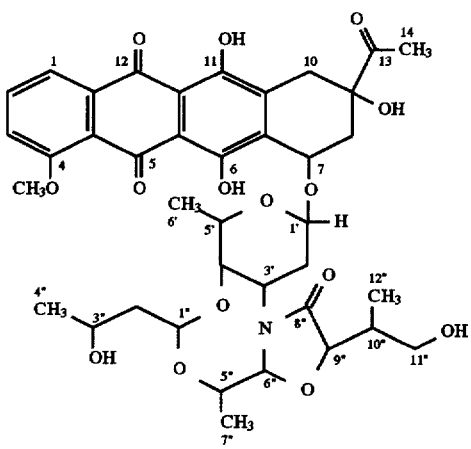

(8) Solubility:

Easily soluble in methanol, ethanol, acetone, chloroform and dimethyl sulfoxide, but hardly soluble in n-hexane, ether and water.

(9) Melting point: 153°–155° C.

(10) High performance liquid chromatography:

A peak is given at a retention time ($t_R$) of 6.9 minutes under the following analytical conditions.

Column: Inertsil ODS-2, 5 μm (4.6 mm inner diameter× 150 mm in length, product of GL Science Co, Ltd.).

Mobile phase: Acetonitrile/0.05% aqueous solution of trifluoroacetic acid (50:50 v/v).

Flow rate: 1 ml/min.

Detection: 210 nm, 0.04 a.u.f.s.

Test Example 1:

(1) Determination of antibacterial activities of the substance IT-62-B:

Minimum inhibitory concentrations (MICs) of the compound according to the present invention against various bacteria were determined in accordance with the MIC measurement method of *Japan Society of Chemotherapy* (see journal of Chemotherapy, Vol. 29, No. 1, pp. 76–79, 1981). More specifically, Muller-Hinton agar media (product of Difco Co.) containing the compound according to the present invention at various concentrations were used. The test organisms diluted to $10^6$ cells/ml, respectively, were inoculated said test organisms having been grown on the same medium as described above. After incubation at 37° C. for 18 hours, the state of growth of the test organisms was observed to take a minimum inhibitory concentration (MIC, μg/ml), at which the growth of the test organism was completely inhibited (in the observation, it was considered that the growth of the test organism was inhibited if the number of colonies was 5 or less.). The results are shown in Table 4.

TABLE 4

| Strain tested | MIC (μg/ml) |
|---|---|
| *Staphylococcus aureus* Smith | 6.25 |
| *Staphylococcus aureus* (MRSA)70 | 12.5 |
| *Staphylococcus aureus* (MRSA)92-1192 | 12.5 |
| *Staphylococcus epidermidis* ATCC 12228 | 25 |
| *Enterococcus faecalis* IFO 12968 | 50 |
| *Micrococcus luteus* ATCC 9341 | 3.13 |
| *Micrococcus luteus* ATCC 10240 | 1.56 |
| *Bacillus subtilis* ATCC 6633 | 3.13 |
| *Bacillus subtilis* ATCC(rec⁺) | 6.25 |
| *Bacillus subtilis* ATCC(rec⁻) | 0.39 |
| *Bacillus cereus* IFO 3001 | 12.5 |

TABLE 4-continued

| Strain tested | MIC (μg/ml) |
|---|---|
| *Escherichia coli* NIHJ | 100 |
| *Escherichia coli* IAM 1268 | 50 |
| *Proteus vulgaris* IID OX-19 | >100 |
| *Klebsiella pneumoniae* ATCC 29665 | >100 |
| *Serratia marcescens* IFO 12648 | >100 |
| *Salmonella typhymurium* G-46 | >100 |
| *Alcaligenes faecalis* IAM 1015 | 12.5 |
| *Pseudomonas aeruginosa* NCTC 10490 | >100 |

Test Example 2:

Determination of antitumor activities of the substance IT-62-B:

A. Determination of 50% inhibitory concentration against the established culture cell line derived from human nasopharyngeal carcinoma:

A 50% inhibitory concentration ($IC_{50}$) of the compound according to the present invention against an established culture cell line (KB cell line) derived from human nasopharyngeal carcinoma was determined. More specifically, the KB cell line ($2\times10^3$ cells/ml of medium) was cultured in an Eagle's minimal essential medium supplemented with a 10% calf serum, and 3 ml of this culture medium was incubated in a plastic Petri dish to incubate it at 37° C. in a $CO_2$-incubator (5% $CO_2$). After overnight incubation, the compound according to the present invention was added with the compound diluted from a concentration of 1 μg/ml to a concentration of $1\times10^{-6}$ μg/ml by 10-fold dilution. After incubation for 3 days, the cells were torn from the surface of the Petri dish with trypsin to count viable cell numbers under an optical microscope by a dye-exclusion method making use of trypan blue, thereby calculating a concentration ($IC_{50}$) exhibiting substantially 50% growth inhibition as compared with a control. As a result, $IC_{50}$ was found to be 0.006 μg/ml.

B. Survival effect against murine leukemia P388 cells implanted intraperitoneally:

The antitumor activity of the compound according to the present invention was judged by the survival effect against murine leukemia (p388 cells). The three of Male $CDF_1$ mice (aged 6 weeks) were used as test animals for an administering group and 10 mice for an untreating control group. Murine leukemia P388 cells ($1\times10^6$ cells) were implanted intraperitoneally in all the mice. Upon elapsed time of 1 day (the first day) after the implantation, the substance IT-62-B dissolved in a 3.5% solution of dimethyl sulfoxide in physiological saline was administered intraperitoneally to the mice of the administering group at a dose of 0.25 mg/kg so as to observe survival days of the mice. Percent increase in survival was calculated from the respective survival days thus obtained in accordance with the following equation, and found to be 119%.

Percent increase in survival =

[(Average survival days of the administered group/

Average survival days of the untreated control group) – 1] × 100 (%)

Results:

As appeared in Test Example 1, the substance IT-62-B according to the present invention exhibited good antibacterial activities against gram-positive bacteria and some of gram-negative bacteria. Besides, as demonstrated by Test Example 2, the compound according to the present invention had the 50% inhibitory concentration ($IC_{50}$) of 0.006 μg/ml against the established culture cell line (KB cell line)

derived from human nasopharyngeal carcinoma, and exhibited the percent increase of 119% in the survival of the mice in which the murine leukemia P388 cells had been implanted intraperitoneally. Therefore, the compound exhibited strong antitumor activities in both in vitro and in vivo tests.

INDUSTRIAL APPLICABILITY

The substance IT-62-B according to the present invention has good antibacterial activities against gram-positive bacteria and some of gram-negative bacteria, and also possesses excellent antitumor activities against tumors such as human nasopharyngeal carcinoma, and is hence useful as a medicine.

We claim:

1. A substance IT-62-B represented by the following formula (1):

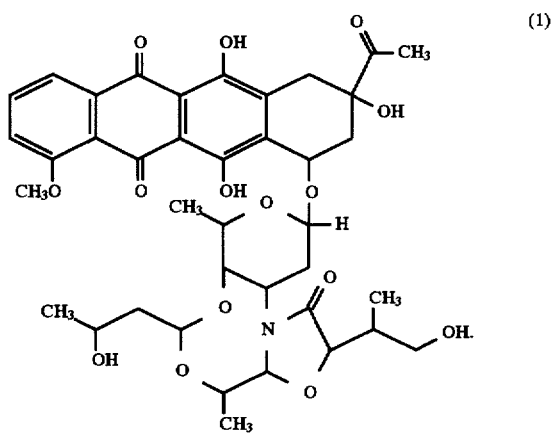

2. A process for producing the substance IT-62-B according to claim 1, which comprises culturing a microorganism belonging to genus Streptomyces and having capability of producing the substance IT-62-B according to claim 1 to produce and accumulate such a compound in the culture fluid and to separate the compound.

3. The process according to claim 2 for producing the Substance IT-62-B, wherein the microorganism is a *Streptomyces sp.* strain IT-62.

4. A medicine comprising the substance IT-62-B as an active component.

5. The medicine according to claim 4, wherein the medicine is an agent for treating a bacterial infectious disease or a tumor.

6. A medicinal composition comprising an effective amount of the substance IT-62-B according to claim 1 and a pharmaceutically permissible carrier.

7. The medicinal composition according to claim 6, which is suitable for use in the treatment for a bacterial infectious disease or a tumor.

8. A method of treating a bacterial infectious disease, which comprises administering an effective amount of the substance IT-62-B according to claim 1 to a patient.

9. A method of treating a tumor, which comprises administering an effective amount of the substance IT-62-B according to claim 1 to a patient.

* * * * *